United States Patent [19]

Uchida

[11] 4,295,830
[45] Oct. 20, 1981

[54] MOTORIZED DENTAL HANDPIECE
[75] Inventor: Sakae Uchida, Machida, Japan
[73] Assignee: Setagayaseiki Co. Ltd., Tokyo, Japan
[21] Appl. No.: 134,254
[22] Filed: Mar. 26, 1980
[30] Foreign Application Priority Data
Nov. 14, 1979 [JP] Japan ................................ 54/147493
[51] Int. Cl.³ .............................................. A61C 1/12
[52] U.S. Cl. .................................................. 433/115
[58] Field of Search ........................................ 433/115
[56] References Cited
U.S. PATENT DOCUMENTS
1,678,097 7/1928 Andresen ............................ 433/115
3,758,948 9/1973 Bareth ................................ 433/115

Primary Examiner—Robert Peshock
Attorney, Agent, or Firm—Jordan and Hamburg

[57] ABSTRACT

A motorized dental handpiece has a head and a head cap portion which is connectable thereto. The head cap portion includes a head gear shaft, a head gear rotatable with the head gear shaft, a head cap, a flange rotatable with the head gear shaft, and a seal ring positionable between the head cap and the flange. The head gear shaft, head cap, seal ring and flange constitute releasably connected members of a unitary head cap portion assembly which is releasably connectable to the head of the handpiece.

3 Claims, 5 Drawing Figures

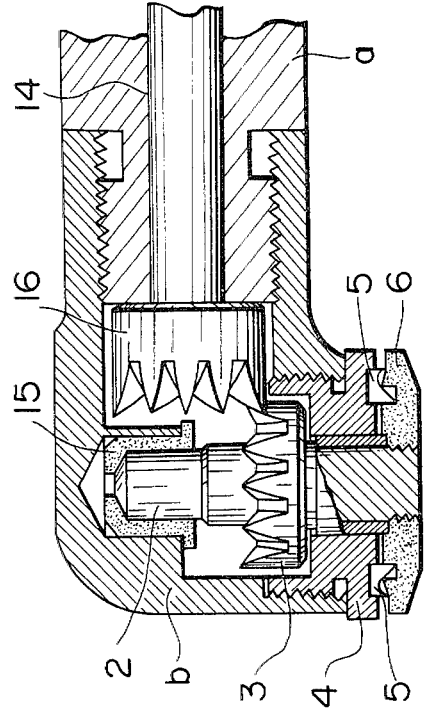
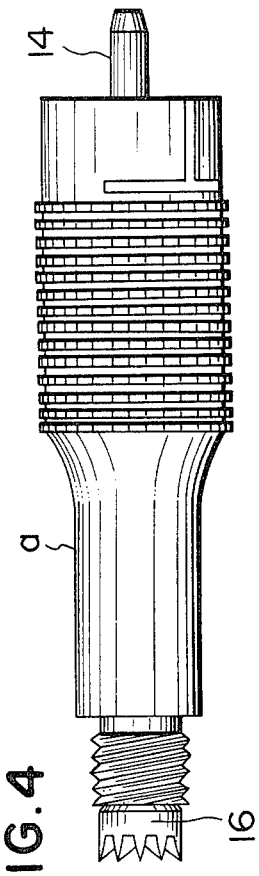
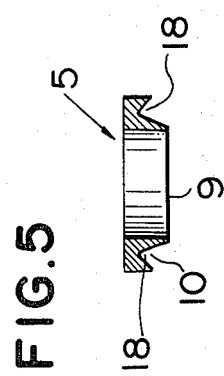
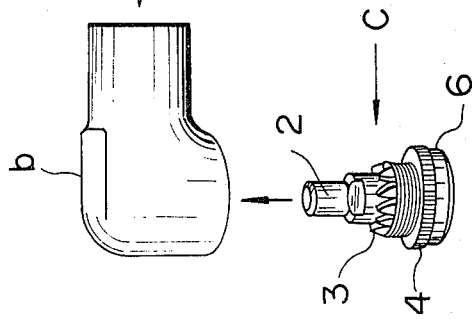
FIG.3  FIG.4  FIG.5

MOTORIZED DENTAL HANDPIECE

BACKGROUND OF THE INVENTION

The present invention relates generally to motorized dental handpieces and more particularly to electrically driven handpieces. Hitherto, motorized dental handpieces for the finishing or abrasion of teeth and associated material by means of a rotatable cutting tool, abrasive disk, rubber caps, etc. have conventionally been composed of a body, a central drive gear, a head, a bearing, a head gear shaft, a drivable head gear, a head cap and a flange. The head gear shaft mounted at the head end portion of the handpiece, the head gear, the head cap and the flange have conventionally been constructed so as to be integral with one another by being press-fit into an independent part which is incapable of being disassembled.

Therefore, it was necessary to replace the whole integrated part when only the seal ring, for example, becomes worn and requires replacement.

The present invention provides a handpiece which enables disassembly of the parts mounted at the head end portion of the handpiece, and also provides a complete water proof and dust proof structure in the gap between the head cap and the flange.

SUMMARY OF THE INVENTION

An object of the present invention is to provide a novel motorized dental handpiece in which the parts mounted at the end portion of the handpiece are constructed so as to be disassembled one from another in order to avoid the need to replace all of such parts due to the wear of only the seal ring.

Another object of the present invention is to provide a construction in which the gap between the head cap and the flange is rendered water proof and dust proof.

BRIEF DESCRIPTION OF THE DRAWINGS

FIG. 3 is a fragmentary front cross-sectional view of the head end of the dental handpiece;

FIG. 4 is a perspective exploded view of the dental handpiece showing an assembling order of the parts; and FIG. 5 is a cross-sectional view of a seal ring.

DETAILED EXPLANATION OF THE INVENTION

In order to attain the above-mentioned objects, the head gear shaft, head cap and flange may be disassembled, and the seal ring which is held between the flange and head cap may easily be replaced by removal of the flange from the head gear shaft. Furthermore, the surface of the seal ring directly contacts with three portions of the flange to provide a triple-seal water proof and dust proof structure.

Hereinafter, embodiments of the present invention will be described in more detail with reference to the drawings.

Figure 1:
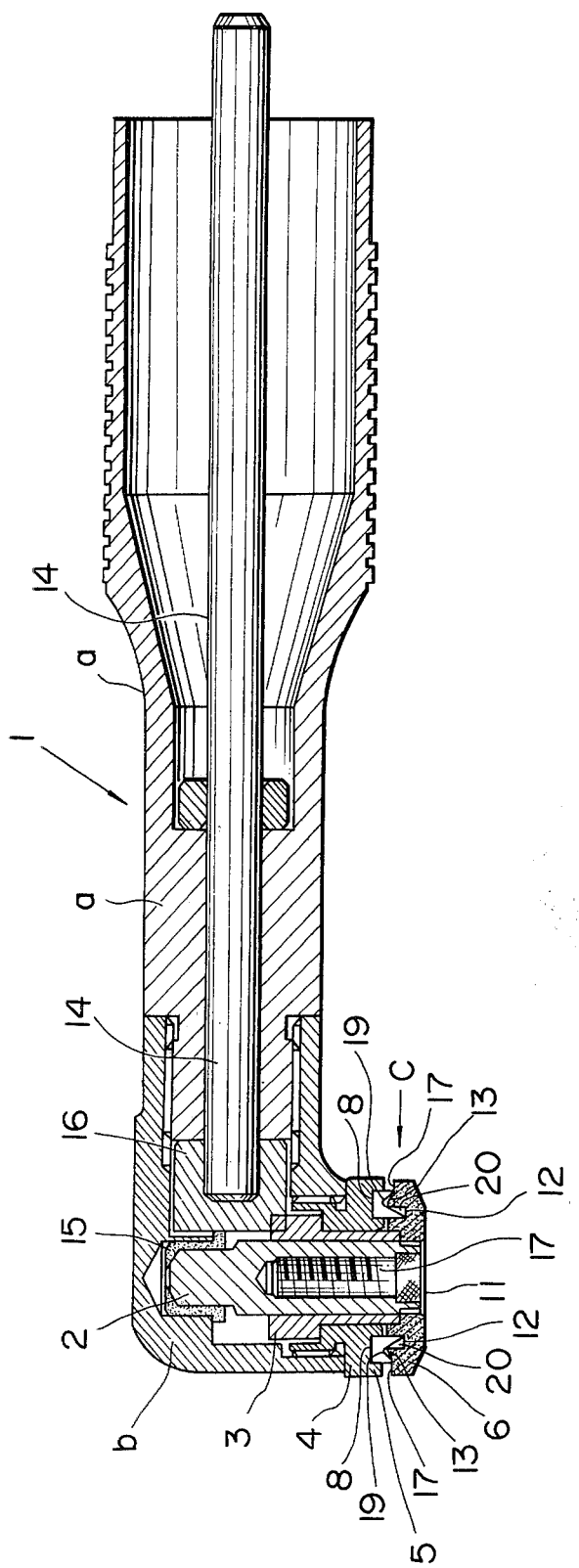
FIG. 1 is a front cross-sectional view of a motorized dental handpiece according to the present invention.
Figure 2:
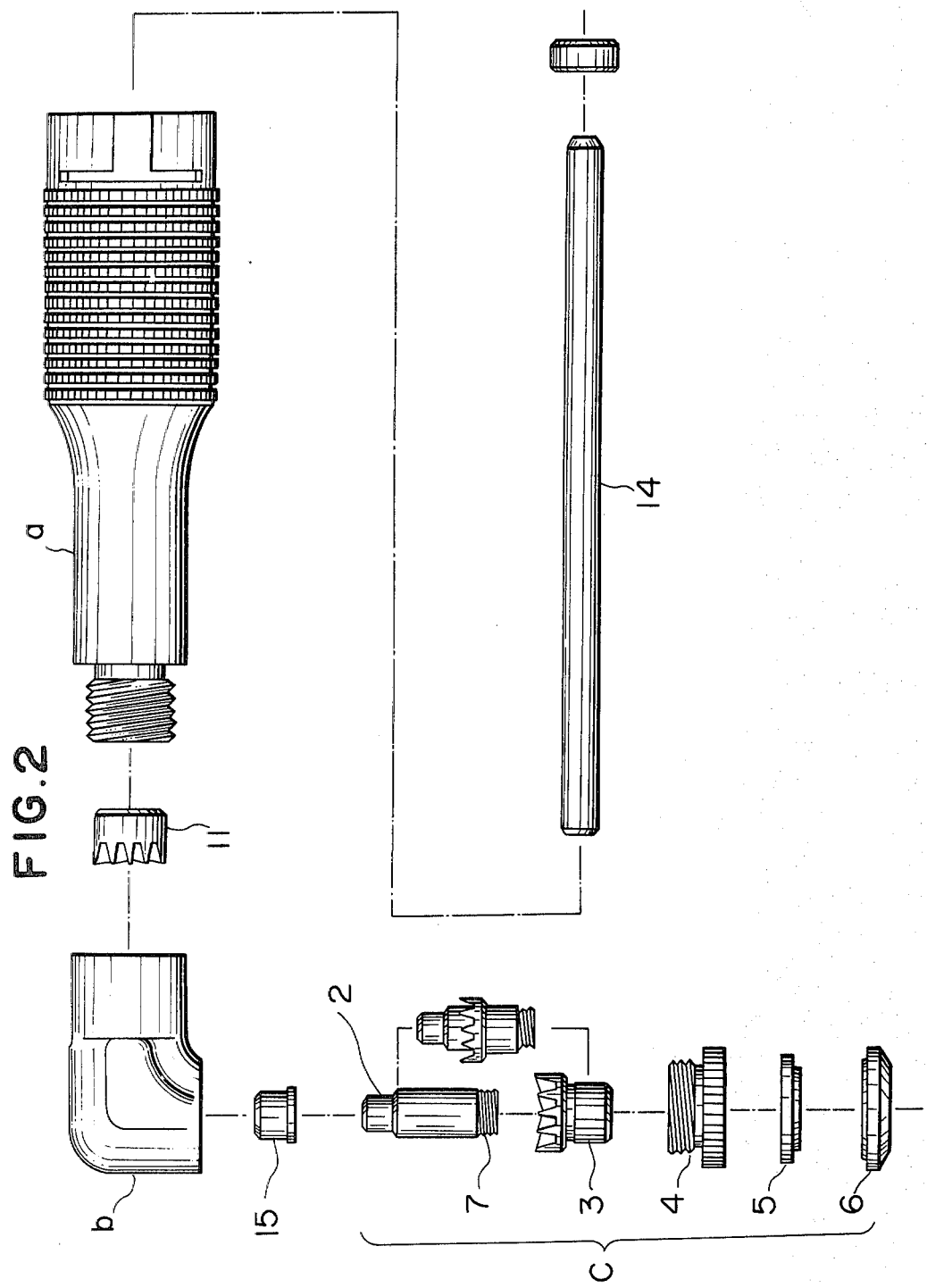
FIG. 2 is a fragmentary exploded elevational view of the dental handpiece of FIG. 1.

FIG. 1 shows a motorized handpiece 1 with cutting equipment according to the present invention. The handpiece consists of a hand-grippable body a, a head b and a head cap portion c. The body of the handpiece and the head b have respectively a conventional structure. The head cap portion c consists of a head gear shaft 2, a head gear 3, a head cap 4, a seal ring 5 and a flange 6. The head gear shaft 2 is given a threaded portion 7 threadably engageable with the flange 6 to be thereby brought into pressing engagement with the head gear 3. On the outer end surface of the head cap 4, a groove 8 is formed to receive seal ring 5. The seal ring is made of fluorine containing rubber which is superior in resiliency characteristics and is resistant against the wear resulting from rotation of the seal ring. V shaped groove 18 is formed on the axially outer peripheral surface of the seal ring thereby providing inner 9 and an outer 10 circumferentially extending edges. The outer edge 10 does not extend axially as far as that of the inner edge 9. The flange 6 is different from a conventional flange and is given a central tapped hole 11 which can threadably engage with the threaded portion 7 of the head gear shaft. Furthermore, a circumferentially extending guide groove 12 is formed on an inner surface of the flange and is engageable with a surface of the inner edge 9 of the seal ring 5 as shown most clearly in FIGS. 1 and 3. The upper portion of the outer peripheral edge of the guide groove is cut to form a circumferentially extending and axially projecting edge 13. The upper horizontal surface of the flange except for the above projecting edge is formed to be a flat surface 17. The head cap portion C is formed by assembling head gear shaft 2, head gear 3, head cap 4 and seal ring 5 and the unitary assembly thus formed is threadably engaged with the head b by means of the head cap 4. The head gear shaft 2 is press-fitted and secured to the inside of the head gear 3 and the head gear shaft 2 is threadably engaged within the tapped hole 11 of the flange 6 with the head cap 4 surmounting the seal ring 5. Thus, the head gear shaft 2 constitutes one part of the head cap portion C. The head cap portion C is secured to the head b by threadably engaging the head cap 4 therewith. The other end of the head gear shaft 2 is thereby fitted within the bearing 15. The rotational effect of an electric motor (not shown) is transmitted to central gear 16 by means of the drive shaft 14 to ultimately rotate the flange 6. Numerical reference 21 identifies a tapped hole within which a cutting tool, an abrasive disk, etc. may be threadably connected and held.

A motorized dental handpiece according to the present invention is composed of the parts as above-mentioned, and it is possible to remove the flange 6 from the head gear shaft 2 so that the replacement of the seal ring 5 may thus be possible, and furthermore it is thereby also easy to clean the dust adhered to the head cap, the seal ring and the flange. When the seal ring 5 is inserted between the head cap 4 and the flange 6, the radially inner wall of the inner edge 9 of the seal ring engages with the whole of the inner peripheral surface of one side of the guide groove 12 formed in the flange. The extremity of the outer edge 10 engages with the flat peripheral surface 17 of the flange, and the extremity of projecting edge 13 of the flange engages with one side of the inner peripheral surface of V shaped groove 18; thereby hollow portions or pockets 19, 20 are formed between the inner peripheral surface of V shaped groove 18 and the adjacent surface of the flange 6. Since the seal ring 5 is fitted to the inside of the head cap 4, the inner peripheral surface of the flange rotates on the peripheral surface of the seal ring 5 maintaining the above-mentioned contacting relationships. Any water or dust entering into the gap formed between the head cap 4 and the flange 6 from the outside is firstly prevented by means of the outer edge 10. Any water or dust passing such edge 10 enters the hollow portion 19 formed by the extremity of the projecting edge 13, the inner peripheral surface of the one side of the V-groove 18 and outer edge 10 to prevent a secondary entering of same into the inside of the cap portion C, and the water or dust entering further from the hollow portion 19 is retained in the hollow portion 20 formed by the projecting edge portion 13, the peripheral surface of the V-groove 18 and inner edge 9 to prevent a tertial entering same into the inside; thereafter a further entering of water or dust into the inside may finally be prevented by the engaging surfaces of one side of the guide groove 12 and the adjacent surface of the inner edge 9. Accordingly a triple water proof and dust proof seal can be obtained by means of the above-mentioned structure so that water or dust will not easily enter. Further, the operational life of the parts of the head cap portion will be increased by preventing substantially completely the entrance of water or dust.

What is claimed is:

1. A motorized dental handpiece having a head and a head cap portion connectable therewith, said head cap portion comprising:

a head gear shaft including a threaded section;
   a head gear rotatable with said head gear shaft;
   a head cap having a threaded section;
   a flange rotatable with said head gear shaft, said flange including a threaded section cooperable with said threaded section of said head gear shaft;
   a seal ring positionable between said head cap and said flange, said head cap being provided with a circumferentially extending groove in the axially outer peripheral surface thereof for reception of the axially inner portion of said seal ring, said flange being provided on the axially inner surface thereof with a circumferentially extending guide groove for reception of the axially outer portion of said seal ring, said seal ring having a V-shaped groove formed in the outer peripheral surface thereof and thereby forming radially inner and outer circumferentially extending edges, said edges being engageable with opposing surfaces of said flange, a wall of said seal ring proximate said radially inner edge thereof being at least coextensive and engageable with the radially inner wall of said guide groove, said regions of engagement thereby providing a plurality of circumferential seals preventing the admission of water and dust to the interior of said cap portion;

said head gear shaft, head cap, seal ring and flange constituting releasably connected members of a unitary head cap portion assembly, said cap portion assembly being releasably connectable to the head of the handpiece, said threaded section of said head cap being cooperable with a threaded section on the head of the handpiece for releasably connecting said unitary assembly thereto.

2. A dental handpiece according to claim 1, wherein the upper extremity of the radially outer wall of said guide groove is configured to form a projecting edge, an upper flat horizontal peripheral edge surface of said flange merging into said projecting edge and extending radially outwardly therefrom, said radially outer edge of said seal ring engaging with said flat horizontal surface of the flange and said projecting edge of the flange engaging with the lower peripheral surface of said seal ring intermediate said inner and outer edge thereof to thereby form a pair of radially spaced pockets.

3. A dental handpiece according to claim 1, wherein said head gear shaft is press-fit into said head gear upon the threading engagement of said head gear shaft and flange.

* * * * *